United States Patent [19]

Schmidtke et al.

[11] Patent Number: 5,457,535
[45] Date of Patent: Oct. 10, 1995

[54] METHOD AND APPARATUS FOR DETERMINING THE CONCENTRATION OF OPTICALLY-ACTIVE MATERIALS IN A FLUID

[75] Inventors: Gerhard Schmidtke, Freiburg; Wolfgang Riedel, Neuenburg; Helmut Wolf, Merzhausen, all of Germany

[73] Assignee: Siemens Aktiengesellschaft, Munich, Germany

[21] Appl. No.: 218,689

[22] Filed: Mar. 28, 1994

Related U.S. Application Data

[63] Continuation of Ser. No. 937,506, Aug. 28, 1992.

[30] Foreign Application Priority Data

Aug. 28, 1991 [DE] Germany ............ 41 28 458.5

[51] Int. Cl.$^6$ .................... G01J 4/00; A61B 5/00
[52] U.S. Cl. .................... 356/364; 356/436; 128/633
[58] Field of Search .................... 356/364–370, 356/432, 433, 435, 436, 300, 305, 319, 322, 327, 330; 250/225, 573; 128/632–634, 664

[56] References Cited

U.S. PATENT DOCUMENTS

| | | |
|---|---|---|
| 3,741,660 | 6/1973 | Abu-Shumays et al. |
| 4,193,691 | 3/1980 | Fjarlie .................... 356/330 |
| 4,467,204 | 8/1984 | Kysilka et al. ............ 356/368 |
| 4,699,514 | 10/1987 | Schmidt et al. .......... 356/367 |
| 4,822,169 | 4/1989 | Distl et al. .............. 356/364 |
| 4,912,059 | 3/1990 | Newman et al. ........ 356/364 |
| 4,988,199 | 1/1991 | Paul ...................... 356/368 |
| 5,009,230 | 4/1991 | Hutchinson ............. 356/368 |
| 5,357,960 | 10/1994 | Schmidtke et al. ...... 356/364 |

FOREIGN PATENT DOCUMENTS

| | | |
|---|---|---|
| 387858 | 3/1989 | Austria . |
| 0144115 | 1/1990 | European Pat. Off. . |
| 2513937 | 10/1976 | Germany . |
| 3908114 | 2/1990 | Germany . |
| 626723 | 11/1981 | Switzerland . |

Primary Examiner—Hoa Q. Pham
Attorney, Agent, or Firm—Hill, Steadman & Simpson

[57] ABSTRACT

In a method and apparatus for determining the concentration of optically-active substances in a fluid, such as glucose in the body fluids of a patient, two light sources are used to produce respective polarized light beams which pass through the substance to be analyzed and are incident on a detector. The second beam has a fixed polarization direction relative to the first beam. The light sources are alternatingly switched on and off at a known-frequency. A dispersing element is disposed in the path of each beam. A comparative signal is produced from the beams exiting the substance and incident on the detector. Due to the presence of the dispersive element in the path of each beam, it is possible to spectrally resolve the components of the comparative signals, so that the optical polarization contributed to the comparative signal by each substance in the fluid can be identified, and thus the concentration of a selected optically-active substance, even in the presence of multiple optically-active substances in the fluid, can be accurately identified.

19 Claims, 2 Drawing Sheets

METHOD AND APPARATUS FOR DETERMINING THE CONCENTRATION OF OPTICALLY-ACTIVE MATERIALS IN A FLUID

This is a continuation of application Ser. No. 07/937,506, filed Aug. 28, 1992, now abandoned.

BACKGROUND OF THE INVENTION

1. Field of the Invention

The present invention is directed to a method and apparatus, using polarimetry techniques, for the quantitative determination of the concentration of optically-active substances in a carrier, such as glucose in body fluids of a patient.

2. Description of the Prior Art

A known technique for determining the concentration of a substance in a fluid carrier is to generate comparative signal, such as a differential or quotient signal, from respective linearly polarized light beams generated by two light sources. The light beams pass through the fluid to be analyzed, and are incident on a detector. One of the linearly polarized light beams has a direction of polarization which is different from the polarization direction of the other light beam by a predetermined angle. The two light sources are alternatingly switched on and off at a predetermined frequency. The measurement signals produced by the detector, corresponding to the two linearly polarized light beams incident thereon, can be used to generate one or more comparative signals, such as difference or quotient signals. Such a polarimetry method and apparatus are described in German Reference 39 08 114. The method and apparatus disclosed therein permits the identification of the concentration of an optically-active substance in a carrier fluid while reducing the influence of interference, such as from aging of the components which comprise the concentration. This known apparatus and method, however, have the disadvantage of permitting only the acquisition of the sum total of the optical polarizations in the light emerging from the carrier being measured. If other substances are present in the path of the light beam in the carrier, which contribute optical polarizations of their own to the sum total, in addition to the polarization contributed by the optically-active substance whose concentration is to be identified, the concentration derived from the sum total may inaccurately represent the true concentration of the substance in question, due to the presence of the polarizations produced by other substances in the carrier.

SUMMARY OF THE INVENTION

It is an object of the present invention to provide a method and apparatus, using polarimetry techniques, which permit the accurate identification of the concentration of a given optically polarizing substance in a light-transmissive carrier, even in the presence of other optically polarizing substances in the light beam path in the carrier.

The above object is achieved in accordance with the principles of the present invention in a method and apparatus wherein the absorption level at a variety of wavelengths in the light emerging from the carrier is identified by a multichannel, spectrally resolving detector. This is facilitated by placing a light dispersing element in the path of each beam. Using data acquired from a reference fluid, the concentration of a given substance which polarizes in the carrier fluid can be determined by determining the degree to which the reference absorption levels have been diminished or extinguished in the light emerging from the carrier fluid. This information can then be used to take the concentration values of all substances in the carrier fluid into account to generate a corrected comparative signal, which can then be further analyzed, as needed, in the standard manner. Using this corrected comparative signal, however, results in a more accurate identification of the concentration of a given substance, since the effects of the polarization contribution made by other substances present in the carrier fluid have been substantially eliminated.

As noted above, the ability to spectrally resolve the emerging light signal is facilitated by the placement of at least one dispersing element in the path of the light beams. The detector is in the form of a line detector in the plane of the angle of refraction or the angle of diffraction of the dispersing element. The optical outputs of the detectors are interfaced with electronic control and processing devices, by means of the spectral "signatures" of each constituent of the carrier fluid can be acquired. From these signatures, the concentrations of the substances which may interfere with the calculation of the concentration of the substance in question can then be determined.

Each spectral "signature" has an associated optical polarization value (which varies with the concentration of the particular substance) which is stored in the electronic control and processing devices. It is then possible to generate a corrected control signal, by calculating a sum or difference signal, using the values for optical polarization of one or more optically polarizing substances which have been stored.

The measurement beam and the reference beam may be dispersed using, for example, a prism-like cuvette, which permits the optical polarizations for various substances in the carrier fluid to be calculated. If the substance in question is the concentration of glucose in body fluids, for example, the concentration value obtained in this manner can be used as a control signal for an implantable insulin pump, which takes into consideration the presence of other substances in the body fluids.

By spectrally dispersing both the measurement light beam and the reference beam, a corrective signal can be calculated for substances which have a high probability of being contained in the fluid being analyzed. These corrected signals are then added or subtracted from the comparative signal which represents the sum total optical polarization generated by all substances contained in the fluid being measured. This corrected signal then contains substantially only the optical polarization generated by the particular substance in question. As a result, the influence of the other optically polarizing substances present in the fluid, which could falsify the measured value of the substance in question, is greatly reduced.

DESCRIPTION OF THE PREFERRED EMBODIMENTS

Figure 1:
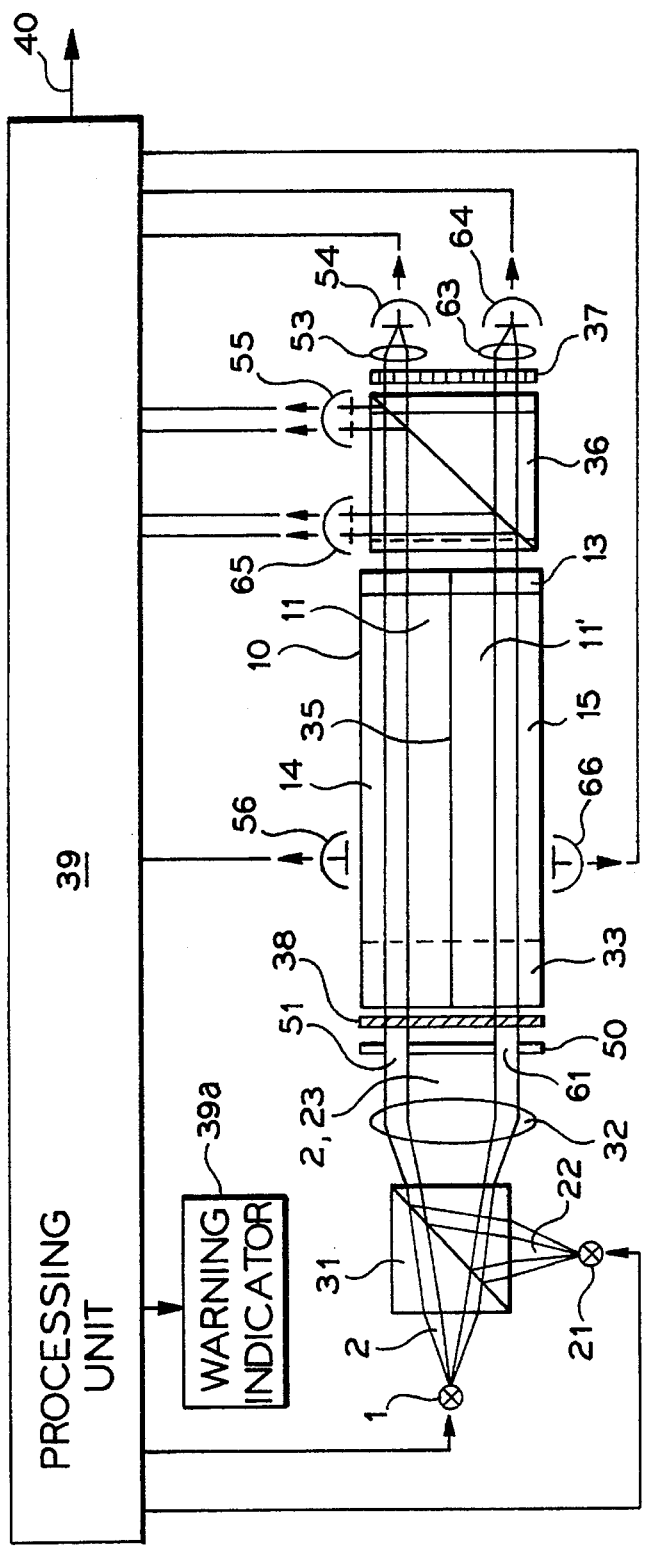
FIG. 1 is a schematic diagram of an apparatus for determining the concentration of optically-active substances, in a carrier fluid, constructed in accordance with the principles of the present invention, and operating according to the method of the invention.

An apparatus constructed in accordance with the principles of the present invention is shown in schematic plan view in FIG. 1. The apparatus is for undertaking a quantitative determination of the concentration of optically refracting and optically absorbing substances, in a light-transmissive carrier medium, such as a carrier fluid, in a first embodiment. The apparatus has a first wide band light source 1, and a second wide band (polychromatic) light source 21, which emit light at substantially the same wavelengths. The light sources 1 and 21, for example, may be light emitting diodes, operating in the same wavelength range of 400 through 900 nanometers.

Although the respective light beams emitted by the light sources 1 and 21 are both shown in FIG. 1 for illustrative purposes, the light sources 1 and 21 are, in actual operation, driven intermittently in the measurement process, for example, in alternation.

The light sources 1 and 21 respectively produce dispersing light beams 2 and 22 which, after passing through a polarizing beam splitter 31, are changed into respective parallel light beams 3 and 23 by a collimating lens 32. A semi-transparent mirror may alternatively be used instead of the combination of the beam splitter 31 and the collimating lens 32. If used, the semi-transparent mirror must be provided with at least one lens per beam path and one polarizer per beam path, the latter, for example, in the form of a foil.

The light beams 3 and 23 pass through openings 50 and 51 of a beam limiter 50. The beams 3 and 23 then pass through a measurement vessel in the form of a cuvette 10, which has a front wall 12 and a rear wall 13, both of which are transparent to the wavelengths of the light emitted by the light sources 1 and 21.

The cuvette 10 has two chambers 14 and 15 which are separated by a wall 35. These chambers 14 and 15 are disposed parallel to the incoming light beams 3 and 23, and extend from the front wall 12 to the rear wall 13. The first chamber 14 is filled with a carrier fluid 11 containing a substance whose concentration is to be identified, such as a dialysis product, and the second chamber 15 is filled with a reference fluid 11'. It will be understood that the chambers 14 and 15 are respectively provided with inlets and outlets to permit the respective fluids 11 and 11' to flow therethrough, however, such inlets and outlets are not shown in the drawings.

The two chamber cuvette 10 has, for example at the front wall 12, a beveled surface 33, making the cuvette 10 form the body of a prism. Good results can be obtained if a wedge is disposed between the cuvette 10 and the beam limiter 50, to adjust the path of the incoming light, and to increase the spectral separation of the light beams 3 and 23.

Figure 2:
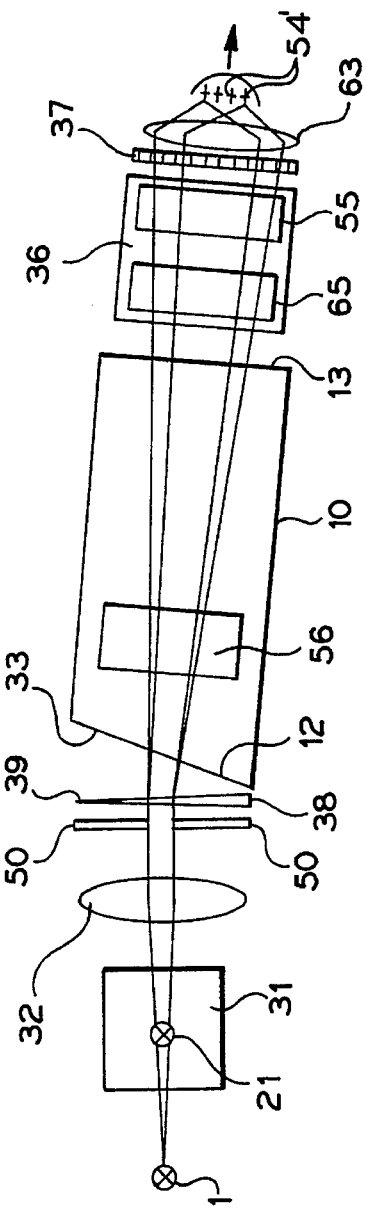
FIG. 2 is a side view of the apparatus of FIG. 1.

The light beams 3 and 23 which have been spectrally separated using the wedge 38 enter the cuvette 10 through the beveled prism surface 33. The surface 33 is displaced by an angle from the normal plane of the propagation axis of the light beams 3 and 23. This angle is defined by the angle of refraction of the wedge 38, schematically indicated by the tip 39 of the wedge 38. The two beams 3 and 23, each of which passes intermittently through both of the chambers 14 and 15, are thus simultaneously absorbed (depending upon the individual wavelength) by the fluids 11 and 11' in the chambers 14 and 15 and are further spectrally split before exiting through the rear wall 13 of the cuvette 10. As can be seen in FIG. 2, the rear wall 13 of the cuvette 10 is disposed in a plane which is substantially normal to the average propagation axis of the expanding light beams 3 and 23. In a further variation of the apparatus, the rear wall 13 may be beveled with respect to the front wall, which enables a larger angle of refraction to be attained by the prism formed by the cuvette 10.

The polarizing beam splitter 31, for example, may be in the form of a beam splitter cube. If so, the light beams 3 and 23 from the light sources 1 and 21 are vertically polarized toward one another. Behind the rear wall 13 of the cuvette 10, a second polarizing beam splitter 36 is used as an analyzer. The second polarizing beam splitter 36 has a polarization plane rotated by 45° compared to the polarization plane of the first polarizing beam splitter 31. Hence, the directions of polarization of the beams 3 and 23 of the light beams which are emitted from light sources 1 and 21 are symmetrical. These polarization directions are, therefore, each disposed at an angle of 45° relative to the directions of passage of light through the analyzer.

The light passing directly through the second polarizing beam splitter 36 thereafter passes through respective converging lenses 53 and 63, and is incident on respective line detectors 54 and 64. The light incident on the line detector 64 has passed through the reference fluid 11', and forms the first reference detector.

The line detector 54, which may also have light incident thereon after passing through the carrier fluid 11, forms an initial measurement data detector. The lines of detector 54 are more easily seen in FIG. 2, wherein the individual measuring elements are designated 54, The detector 64 has similar individual detectors. As can be seen in FIG. 2, the line detectors 54 and 64 lie in the plane of the angle of refraction of the cuvette 10, and the wedge 38. The measurement data signals acquired by the line detectors 54 and 64 are supplied to an electronic processing unit 39. The processing unit 39 may have a measurement value display (not separately shown). The processing unit 39 permits the optical refraction and the absorption characteristics of the various constituent of the carrier fluid (dialysis product) 11 and the reference fluid 11, to be determined. The optical refraction data are calculated based on the position of the individual beam parts on the line detectors 54 and 64, each of which represents a spectral section. The absorption characteristics are determined by comparing the intensity relationships among the individual detectors of the detector lines 54 and 64.

To increase the spectral resolution, a transparent optical grid may be disposed between the second polarizing beam splitter 36 and the converging lenses 53 and 63. It is alternatively possible to use only the grid 37, without the wedge 38, and the cuvette 10 can then have parallel walls 12 and 13. In some instances this results in a reduction in the resolution obtainable by the detector lines 54 and 64, but will avoid the aberration problems introduced by optical elements which are not disposed parallel to each other. In any event, in accordance with the invention at least a dispersing element must be provided in the light path of each of the beams 3 and 23, to ensure that the two beams can be spectrally distinguished from one another by the individual detector elements of the detectors 54 and 64 (and, as explained below, on the individual elements of further detectors 55 and 65).

The converging lenses 53 and 63 are shown in FIG. 1 in an oval form. This is to stress the dispersion which occurs in the two chamber cuvette 10. In practice, the beam path may be made such a size that circular converging lenses 53 and 63 may be used.

Data identifying the optical rotation (polarization) of individual components on the same individual detector 54' of the line detector 54 can be obtained based on the various correlating signals of the intermittently operating light sources 1 and 21. The measurement process is described in detail in German Reference 39 08 114, and in particular as shown in FIG. 2 of that document. As described therein, difference and quotient measurement signals are calculated by intermediate storage of the optical signal currents, and these difference and/or quotient signals are then used to determine the concentration of the optically-active substance in question in the carrier fluid 11. Good results are obtained in the determination of the absorption characteristics of various constituents of the carrier fluid (dialysis product) 11 and the reference liquid 11' from the spectrally resolved light beam by comparing the intensity curves among the individual detectors of the respective detector lines 54 and 64. The measured value signal of a particular detector element 54', which is assigned to a given wavelength range, may be allocated to a predetermined substance, and the concentration of that substance in the carrier fluid 11 can then be determined directly by the absorption in the light beam. The concentration of a previously known interference substance (selected by virtue of being likely to appear in the dialysis product 11) is stored in the electronic processing unit 39 as an optical polarization value. This is contained in the total optical polarization value (calculated as described below) and corresponds to the concentration of the substance in question.

The relationship between the "signatures" of the two optical polarization values determines whether the interference substance is producing a polarization component in the same direction as the optical polarization value of the substance in question, or produces an oppositely directed polarization value. In the former instance, the polarization component contributed by the interference substance must be subtracted from the total optical polarization signal, and in the latter instance, it must be added to the total signal. For example, using line detectors 54 and 64 each having 100 individual detectors, it is possible to determine the interference concentration of many known, predetermined substances, which are either probably or certainly contained in the carrier fluid (dialysis product) 11. Using these additional values of optical polarization (rotation), the total polarization (rotation) value of the carrier fluid 11 can be corrected so that substantially only the optical polarization value, caused, for example, by glucose remains. Glucose is not self-absorbing, and is therefore capable of being spectrally resolved.

The light beams from the light sources 1 and 21, diverged by the beam splitter 36, are incident on additional detectors 55 and 65 at a particular position. The detectors 55 and 65 may consist of two semi-circular detector elements (not separately shown in the drawing). Hence, by comparing the two signals with one another, and even given the smallest of deviations, the dispersion in question can be determined. This result is more accurate than using line detectors 54 and 64 exclusively, because those detectors have a large number of individual detector elements in order to be sensitive over a wide wavelength range. For example, in the case of long-term implantation of an apparatus of this type in a patient, differences in sensitivity can arise, which cannot be compensated, and which could falsify the measurement result. Having determined the dispersion using the detectors 55 and 65, the spectral measuring range of the line detectors 54 and 64 can then be calibrated.

The total optical polarization value of the carrier fluid (dialysis product) 11 is determined by comparing the two halves of the second measurement detector 55 with the signal from the second reference detector 65. Using this as a basis, as described above, the corresponding corrected rotation values are subtracted in the processing unit 39 in accordance with the interference substance concentrations determined from the absorption measurements. This then gives the concentration of the substance in question, for example, glucose. Such interference substances, as described above, which strongly polarize, are particularly likely to be antibiotics, which may rotate the light in both directions and have signal strength which may comprise as much as 10% to 50% of the total measured signal.

Furthermore, stray light detectors 56 and 66 are provided on the long sides of the chambers 14 and 15 of the cuvette 10. The measurement of stray light by the detectors 56 and 66 is for the following reason. If the carrier fluid 11 is a dialysis product, it will also contain protein molecules. The larger protein molecules, particularly those having a mass of more than 5000 a.u., are normally kept out of the cuvette 10 as the carrier fluid (dialysis product) 11 is circulated thereto, for example, through a filter. Protein molecules having a mass of less than 5000 a.u. may, however, cause a degree of optical polarization which can amount to 10% of the glucose component of the optical polarization signal. These molecules disseminate in the light beams passing through the cuvette 10, and thus cause stray light to emerge from the sides thereof. The concentration of the protein molecules present in the cuvette 10 can thus be determined by measuring the intensity of the stray light. The resulting value of optical rotation (polarization) caused by the protein molecules, which could cause interference, is then subtracted from the calculated value of optical polarization.

What remains in the signal is the optical polarization value of the substance in question, for example, glucose. The interference from the optical polarization values of substances which are not capable of being spectrally identified, such as protein molecules, is mathematically removed from the optical rotation signal obtained from detectors 55 and 65 by measuring the stray light and calculating the value of optical polarization of absorbing substances based on the signals from the line detectors 54 and 64. Good results in improving the measurement sensitivity are obtained using the "lock-in" technology described in the aforementioned German Reference 39 08 114. As described therein, light sources which intermittently emit at, for example, a maximum of a few kilohertz are additionally modulated using a modulation frequency which is at least as large as the initial modulation frequency.

Figure 3:
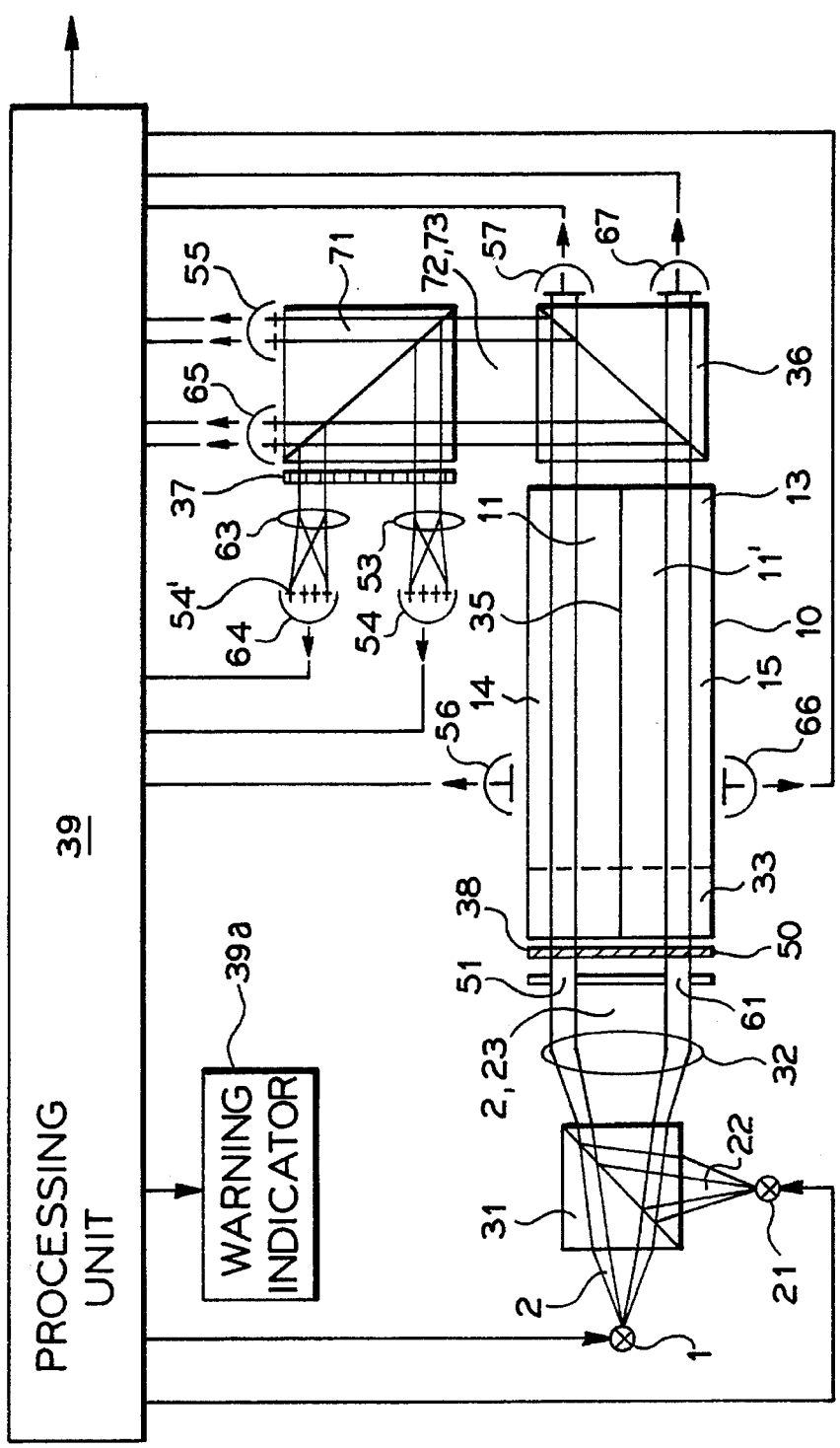
FIG. 3 is a schematic view of a further embodiment of an apparatus for determining the concentration of an optically-active substances in a carrier fluid constructed in accordance with the principles of the present invention, and operating according to the method of the invention.

A further embodiment of the apparatus according to the invention is shown in FIG. 3. Apparatus components identical to those discussed in connection with FIGS. 1 and 2 have been given the same reference numerals.

In the embodiment of FIG. 3, the direction of the beam emerging from one side of the second beam splitter 36 is changed by a further beam splitter 71, in the form of a beam splitter cube, located directly behind the cuvette 10. The further beam splitter 71 transmits light beams 72 and 73 to the detectors 54 and 64, wherein the beams are spectrally analyzed, as well as to detectors 55 and 65 where the dispersion and the total optical polarization signal are determined. Operation of these detectors, and the use of the signals therefrom, is as previously described in connection with FIGS. 1 and 2. In the embodiment of FIG. 3, the beams which pass directly through the second beam splitter 36 are incident on respective detectors 57 and 67, of which detector 67 forms the reference detector. These detectors are used to directly measure the total optical polarization value of the optically polarizing substances contained in the carrier fluid (dialysis product) 11. In the embodiment of FIG. 3, the detectors 55 and 65 are in semi-circular form. The signals from the detectors 55 and 65 in the embodiment of FIG. 3 can, for simplicity, be omitted from the calculations which are undertaken by the processing unit 39, and the detectors 55 and 65 used exclusively to measure the refraction which is then used to assign the appropriate spectral ranges to the individual detector elements of the line detectors 54 and 64. The use of the four detector pairs 54 and 64, 55 and 65, 56 and 66 and 57 and 67 is, however, still desirable. Although the signals from these detectors are partially used for the determination of redundant values, this is still desirable from the standpoint of long-term stability, since it is the intention that the apparatus will be implanted into a human and therefore surgery to remove and/or exchange devices should be avoided.

The processing unit 39 may include a threshold detector which compares the intensity of the stray light as measured by detectors 56 and 66 to a threshold, which may be programmable. If the detected stray light intensity exceeds the threshold, a warning indicator 39a is activated.

The light sources 1 and 21 may alternatively be incandescent lamps, in which case a beam chopper may be used to produce the intermittent beams.

Although modifications and changes may be suggested by those skilled in the art, it is the intention of the inventors to embody within the patent warranted hereon all changes and modifications as reasonably and properly come within the scope of their contribution to the art.

We claim as our invention:

1. In an apparatus for determining the concentration of optically-active substances, by polarimetry, in a carrier medium, the apparatus having a measurement vessel with two separated chambers in which said carrier medium and a reference medium are respectively disposed, to polychromatic light sources which generate respective light beams in respective propagation paths light beams, and means for identifying the concentration of a selected substance in said carrier medium by generating a comparative signal based on the respective resulting polarization arising in said light beams due to interaction with said carrier and reference media, said vessel having side walls which are transmissive for said light beams, the improvement comprising:

means disposed in the respective propagation paths of said light beams for dispersing said light beams before said light beams are incident on said detector means and for thereby causing substance-dependent interaction of said light beams in said carrier and reference media;

means for identifying the concentration of a selected substance in said carrier medium by generating a comparative signal based on the respective resulting polarization arising in said light beams due to interaction with said carrier and reference media, and stray light detector means disposed on opposite sides of said measurement vessel for detecting stray light from said light beams deflected through said side walls of said measurement vessel by non-absorbing molecules in said carrier medium and for generating an electrical signal corresponding to said stray light for use by said means for identifying the concentration of said selected substance in the generation of said comparative signal to correct said comparative signal dependent on the magnitude of the detected stray light.

2. The improvement of claim 1 wherein said measurement vessel has an optical axis defined by the average of said propagation paths of said light beams therethrough, and wherein said means for dispersing said light beams is a means for refracting said light beams at an angle of refraction, said means for refracting having a surface disposed in a plane at said angle of refraction relative to said optical axis.

3. The improvement of claim 2 wherein said means for refracting said light beams is a beveled surface of said measurement vessel disposed at a side of said measurement vessel through which said light beams enter said measurement vessel.

4. The improvement of claim 2 wherein said means for refracting is a wedge disposed between said light sources and said measurement vessel.

5. The improvement of claim 1 wherein said means for dispersing said light beams is a means for diffracting said light beams.

6. The improvement of claim 5 wherein said means for diffracting said light beams is a diffraction grid disposed between said measurement vessel and said detector means.

7. The improvement of claim 1 further comprising:

means for splitting said light beams emerging from said chambers into first beams, which are incident on said detector means, said detector means constituting first detector means, and into second beams; and second detector means on which said second beams are incident for generating signals used by said means for identifying the concentration of said selected substance in the generation of said comparative signal.

8. The improvement of claim 7 wherein said second detector means consists of two semi-circular detectors which generate output signals corresponding to the dispersion of said light beams.

9. The improvement of claim 7 further comprising:

means for splitting said second beams for generating third beams, said second beams passing through said means for splitting said second beams onto said second detector means; and third detector means on which said third beams are incident for generating further signals used by said means for identifying the concentration of said selected substance in the generation of said comparative signal.

10. The improvement of claim 1 further comprising:

means for determining whether the amount of said non-absorbing molecules in said carrier medium exceeds a predetermined threshold based on said signals from said means for detecting stray light; and means for generating a warning if said threshold is exceeded.

11. In a method for determining the concentration of optically-active substances, by polarimetry, in a carrier medium, including the steps of directing respective light beams from two polychromatic light sources in respective propagation paths passing through both a carrier medium and a reference medium respectively contained in separate chambers of a measurement vessel having side walls which are transmissive for said light beams and wherein said respective light beams interact with said carrier and reference media such that polarization occurs, detecting said light beams upon emerging from said chambers and generating electrical signals corresponding to characteristics of said light beams, and means for identifying the concentration of a selected substance in said carrier medium by generating a comparative signal based on a respective resulting polarization arising in said light beams due to interaction with said carrier and reference media, the improvement comprising:

passing said light beams through a dispersing element for dispersing said light beams before said light beams are incident on said detector means;

identifying the concentration of a selected substance in said carrier medium by generating a comparative signal based on a respective resulting polarization arising in said light beams due to interaction with said carrier and reference media; and detecting stray light from said light beams deflected through said walls of said measurement vessel by non-absorbing molecules in said carrier medium and generating an electrical signal corresponding to said stray light for use for identifying the concentration of said selected substance in the generation of said comparative signal by correcting said Comparative signal dependent on the magnitude of the detected stray light.

12. The improvement of claim 11 wherein said measurement vessel has an optical axis defined by the average of said propagation paths of said light beams therethrough, and wherein the steps of dispersing said light beams is further defined by refracting said light beams at an angle of refraction, by directing said beams at a surface disposed in a plane at said angle of refraction relative to said optical axis.

13. The improvement of claim 12 wherein the steps of refracting said light beams is further defined by refracting said light beams with a beveled surface of said measurement vessel disposed at a side of said measurement vessel through which said light beams enter said measurement vessel.

14. The improvement of claim 12 wherein the step of refracting said light beams is further defined by refracting said light beams with a wedge disposed between said light sources and said measurement vessel.

15. The improvement of claim 11 wherein the steps of dispersing said light beams is further defined by diffracting said light beams.

16. The improvement of claim 15 wherein the steps of diffracting said light beams is further defined by diffracting said light beams with a diffraction grid disposed between said measurement vessel and a detection location for said light beams.

17. The improvement of claim 11 comprising the additional steps of:

splitting said light beams emerging from said chambers into first beams and second beams; and separately detecting said first beams and said second beams for generating respective signals used for identifying the concentration of said selected substance in the generation of said comparative signal.

18. The improvement of claim 17 comprising the additional steps of:

splitting said second beams for generating third beams; and separately detecting said third beams for generating further signals used by said means for identifying the concentration of said selected substance in the generation of said comparative signal.

19. The improvement of claim 11 further comprising the additional steps of:

determining whether the amount of said non-absorbing molecules in said carrier medium exceeds a predetermined threshold based on said magnitude of said detected stray light; and generating a warning if said threshold is exceeded.

* * * * *